United States Patent
Lilagan et al.

(10) Patent No.: US 11,290,637 B2
(45) Date of Patent: Mar. 29, 2022

(54) INTELLIGENT MANUAL ADJUSTMENT OF AN IMAGE CONTROL ELEMENT

(71) Applicant: Intuitive Surgical Operations, Inc., Sunnyvale, CA (US)

(72) Inventors: Paul E. Lilagan, Sunnyvale, CA (US); Wenyi Zhao, Weston, FL (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/910,941

(22) Filed: Jun. 24, 2020

(65) Prior Publication Data

US 2020/0322526 A1    Oct. 8, 2020

Related U.S. Application Data

(63) Continuation of application No. 15/938,330, filed on Mar. 28, 2018, now Pat. No. 10,715,720, which is a
(Continued)

(51) Int. Cl.
*H04N 5/232* (2006.01)
*A61B 1/00* (2006.01)
(Continued)

(52) U.S. Cl.
CPC ..... *H04N 5/23216* (2013.01); *A61B 1/00006* (2013.01); *A61B 1/00188* (2013.01);
(Continued)

(58) Field of Classification Search
CPC ....... H04N 5/232125; H04N 5/232945; H04N 5/23218; H04N 5/23212; H04N 5/23293;
(Continued)

(56) References Cited

U.S. PATENT DOCUMENTS 4,251,143 A * 2/1981 Stemme ................ G03B 13/20
250/201.7
5,170,202 A  12/1992 Bell
(Continued)

OTHER PUBLICATIONS

Scharstein D., et al., "High-Accuracy Stereo Depth Maps Using Structured Light," IEEE Computer Society Conference on Computer Vision and Pattern Recognition, 2003, vol. 1, pp. 195-202.
(Continued)

*Primary Examiner* — John W Miller
*Assistant Examiner* — Sean N. Haiem
(74) *Attorney, Agent, or Firm* — Haynes and Boone, LLP

(57) ABSTRACT

A method performed by a processor comprises determining a depth value of a target area relative to the image capturing device. The method also includes determining an adjustment to the brightness control so that a brightness level of images captured by the image capturing device is lowered if the depth value of the target area relative to the image capturing device is less than a threshold depth value. The method also includes determining whether an adjustment of the brightness control is to be automatically or manually adjusted. If the adjustment of the brightness control is to be manually adjusted, the processor over-rides manual control of the brightness control if an operator of the brightness control is causing the brightness level of images not to be lowered if the depth value of the target area relative to the image capturing device is less than the threshold depth value.

18 Claims, 11 Drawing Sheets

Related U.S. Application Data continuation of application No. 14/210,986, filed on Mar. 14, 2014, now Pat. No. 9,948,852.

(60) Provisional application No. 61/794,068, filed on Mar. 15, 2013.

(51) Int. Cl.
*A61B 90/00* (2016.01)
*H04N 5/235* (2006.01)
*H04N 13/204* (2018.01)
*H04N 5/238* (2006.01)
*H04N 13/296* (2018.01)

(52) U.S. Cl.
CPC ........ *A61B 1/00193* (2013.01); *A61B 90/361* (2016.02); *H04N 5/23218* (2018.08); *H04N 5/232125* (2018.08); *H04N 5/232945* (2018.08); *H04N 5/238* (2013.01); *H04N 5/2353* (2013.01); *H04N 13/204* (2018.05); *H04N 13/296* (2018.05)

(58) Field of Classification Search
CPC .. H04N 5/2353; H04N 5/238; H04N 13/0203; H04N 13/0296; H04N 13/204; H04N 13/296; H04N 5/23216; A61B 1/00193; A61B 1/00006; A61B 1/00188
USPC .......................................................... 348/46
See application file for complete search history.

(56) References Cited

U.S. PATENT DOCUMENTS

| | | | | |
|---|---|---|---|---|
| 5,521,671 A | * | 5/1996 | Aoki ...................... | G03B 17/18 396/281 |
| 6,301,441 B1 | * | 10/2001 | Kato ........................ | G02B 7/08 396/131 |
| 6,424,885 B1 | | 7/2002 | Niemeyer et al. | |
| 6,568,809 B2 | | 5/2003 | Trajkovic et al. | |
| 6,659,939 B2 | | 12/2003 | Moll et al. | |
| 6,720,988 B1 | | 4/2004 | Gere et al. | |
| 7,782,392 B2 | | 8/2010 | Yamazaki | |
| 8,027,582 B2 | | 9/2011 | Li | |
| 8,184,880 B2 | | 5/2012 | Zhao et al. | |
| 9,052,569 B2 | * | 6/2015 | Nakata ............. | H04N 5/232123 |
| 9,948,852 B2 | | 4/2018 | Lilagan et al. | |
| 10,715,720 B2 | | 7/2020 | Lilagan et al. | |
| 2002/0173778 A1 | * | 11/2002 | Knopp ............... | B23K 26/0096 606/5 |
| 2003/0019933 A1 | * | 1/2003 | Tsikos .................... | G02B 27/48 235/454 |
| 2005/0043583 A1 | * | 2/2005 | Killmann ........... | A61B 1/00016 600/109 |
| 2005/0254143 A1 | * | 11/2005 | Saito ....................... | G02B 7/102 359/698 |
| 2007/0156017 A1 | | 7/2007 | Lamprecht et al. | |
| 2007/0165027 A1 | * | 7/2007 | Nakadaira ............ | H04N 13/302 345/426 |
| 2009/0245600 A1 | * | 10/2009 | Hoffman ................ | A61B 90/37 382/128 |
| 2010/0008206 A1 | * | 1/2010 | Jeong .................... | G11B 7/1369 369/103 |
| 2011/0150447 A1 | * | 6/2011 | Li ....................... | H04N 5/23212 396/104 |
| 2011/0211045 A1 | * | 9/2011 | Bollano .................. | G06T 7/593 348/46 |
| 2011/0234756 A1 | * | 9/2011 | Adler ...................... | G06T 5/002 348/46 |
| 2012/0121129 A1 | * | 5/2012 | Okamoto ........... | H04N 5/23293 382/103 |
| 2012/0176481 A1 | * | 7/2012 | Lukk .................... | H04N 13/243 348/47 |
| 2012/0206050 A1 | * | 8/2012 | Spero ..................... | F21K 9/232 315/152 |
| 2013/0050426 A1 | * | 2/2013 | Sarmast .................. | G06T 7/521 348/46 |
| 2013/0083199 A1 | * | 4/2013 | Choi .................... | H04N 5/23212 348/164 |
| 2013/0107104 A1 | * | 5/2013 | Uchida .......... | G02B 15/145129 348/340 |
| 2013/0107207 A1 | * | 5/2013 | Zhao .................. | G06K 9/00604 351/206 |
| 2014/0333726 A1 | * | 11/2014 | Tokui ..................... | G06T 7/586 348/46 |
| 2015/0206002 A1 | * | 7/2015 | Ponten ................. | G06T 7/246 382/103 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INTELLIGENT MANUAL ADJUSTMENT OF AN IMAGE CONTROL ELEMENT

CROSS REFERENCE TO RELATED APPLICATIONS

This application is a continuation of U.S. application Ser. No. 15/938,330 (filed Mar. 28, 2018), which is a continuation of U.S. application Ser. No. 14/210,986 (filed Mar. 14, 2014), now U.S. Pat. No. 9,948,852, which claims priority to U.S. provisional Application No. 61/794,068 (filed Mar. 15, 2013), each of which is incorporated herein by reference.

FIELD OF THE INVENTION

The present invention generally relates to imaging systems. In particular, it relates to an imaging system, and a method implemented therein, for providing intelligent manual adjustment of a control element of either an image capturing device or a viewer to provide assistance in achieving a desirable adjustment of the control element that is a function of a depth value of a target area relative to the image capturing device.

BACKGROUND

Imaging systems such as a camera are commonly provided with an autofocus (AF) feature. As described in U.S. Pat. No. 7,782,392 B2, conventional electronic camera systems may provide an autofocus feature using either the contrast (e.g., blur) of the captured image or a determined depth value of an object within the field of view of the camera. The depth value may be determined using reflected light and principles of triangulation. In addition to providing an autofocus feature, automatic exposure control (AE) may also be provided to determine the brightness of the object and adjust exposure. Alternatively, as described in U.S. Pat. No. 6,568,809 B2, a desirable focal point for a binocular or camera may be determined by tracking the gaze of a user's eyes.

In certain applications, however, it may desirable to allow the user to override the autofocus (AF) and/or automatic exposure control (AE) feature. In this case, the user should be allowed to manually adjust a control element such as a focus or brightness control. When the image is out of focus, however, it may not be apparent to the user in which direction adjustment should be made. Accordingly, the user may adjust the control in the wrong direction initially before realizing the error and subsequently changing the direction of the adjustment. Alternatively, the user may adjust the control in the right direction, but overshoot the correct focal point so that a reversal of direction back to correct focal point is required. Such iterative type of manual adjustment, however, is time-consuming. Also, such iterative manual operation of an image control element may require the complete attention of the user so that the user is prevented from attending to other tasks at the time, such as when the camera is part of a robotic system and the user is manipulating one or more tools, as described, for example, in U.S. Pat. No. 6,424,885 B1.

BRIEF SUMMARY

The embodiments of the invention are summarized by the claims that follow below.

DETAILED DESCRIPTION

Figure 1:
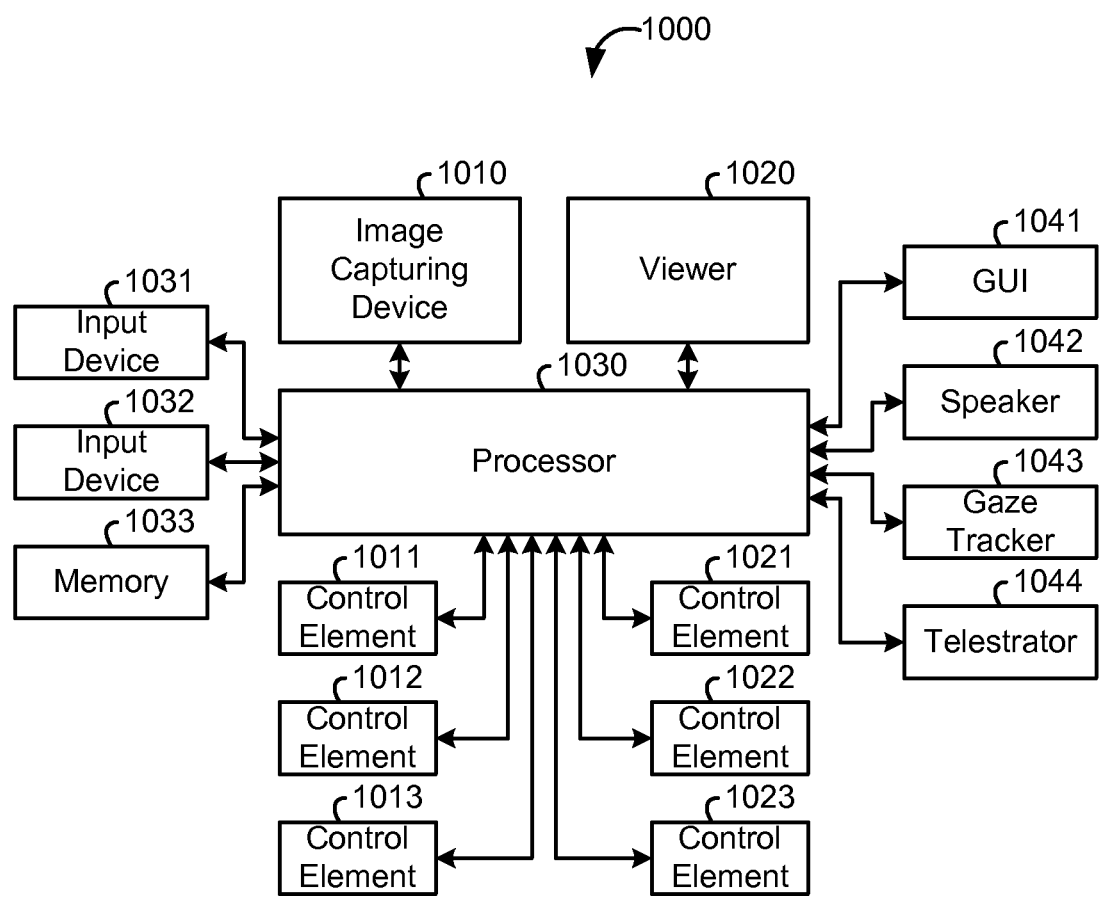
FIG. 1 illustrates a block diagram of an imaging system utilizing aspects of the present invention.

FIG. 1 illustrates, as an example, a block diagram of an imaging system 1000. An image capturing device 1010 is included, which is preferably a high-definition digital stereo camera that generates a video stream of stereo images captured at a frame rate of the camera, such as thirty frames per second. Each frame of stereo images includes a left stereo image and a right stereo image. An example of such a stereo camera is described below in reference to FIGS. 7, 8. Alternatively, the image capturing device 1010 may be a monovision camera or it may be a device using a different imaging modality such as radiography, ultrasound, and magnetic resonance imaging. Although only one image capturing device is shown, the imaging system 1000 may include a plurality of image capturing devices of the same or different types.

A viewer 1020 is included, which is preferably a stereo viewer having left and right display screens for respectively displaying left and right stereo images derived from left and right stereo images captured by the image capturing device 1010. An example of such a stereo viewer is described below in reference to FIG. 10. Alternatively, if the image capturing device 1010 is not a stereo camera, then the viewer 1020 may be monovision viewer suitable for displaying monovision and/or other types of images captured by the image capturing device 1010.

A processor 1030 is included, which performs various functions for the imaging system 1000. For example, the processor 1030 may process the images received from the image capturing device 1010 for display on the viewer 1020. Such processing may include modification of the captured images for different resolutions and for camera distortion and/or misalignment correction. In telerobotic operation, such processing may also include modification of the captured images to provide telepresence.

The processor 1030 also performs a method 2000 as described below in reference to FIG. 2. In doing so, the processor 1030 processes user inputs received from various input devices such as input devices 1031, 1032, a Graphical User Interface (GUI) 1041, a telestrator 1043, a plurality of control elements (e.g., 1011, 1012, 1013) associated with the image capturing device 1010 for adjusting image characteristics or attributes of the captured images, and a plurality of control elements (e.g., 1021, 1022, 1023) associated with the viewer 1020 for adjusting image characteristics or attributes of the displayed images.

Also while performing the method 2000, the processor 1030 may receive information from various sources, such as the input devices 1031, 1032, a gaze tracker 1043, and the memory 1033. The processor 1030 may also generate outputs which it transmits to various devices such as audio output transmitted to a speaker 1042 and haptic or force feedback transmitted to input devices 1031, 1032 and control elements 1011, 1012, 1013, 1021, 1022, 1023 as sensory outputs. The input devices 1031, 1032 may be manually manipulatable like the control elements or they may provide a means for the user to interact with the processor 1030 such as a keyboard or mouse. Alternatively, one or both of the input devices 1031, 1032 may respond to other user initiated stimuli such as voice commands. Although only two input devices are shown in FIG. 1, it is to be appreciated that more or less input devices may be included in the imaging system 1000.

Additional details on a telestrator such as the telestrator 1044 may be found, for example, in U.S. 2007/0156017 entitled "Stereo Telestration for Robotic Surgery", which is incorporated herein by reference. Additional details on such a gaze tracker such as the gaze tracker 1043 may be found, for example, in U.S. Application No. 61/554,741 entitled "Method and System for Stereo Gaze Tracking", which is incorporated herein by reference.

Figure 2:
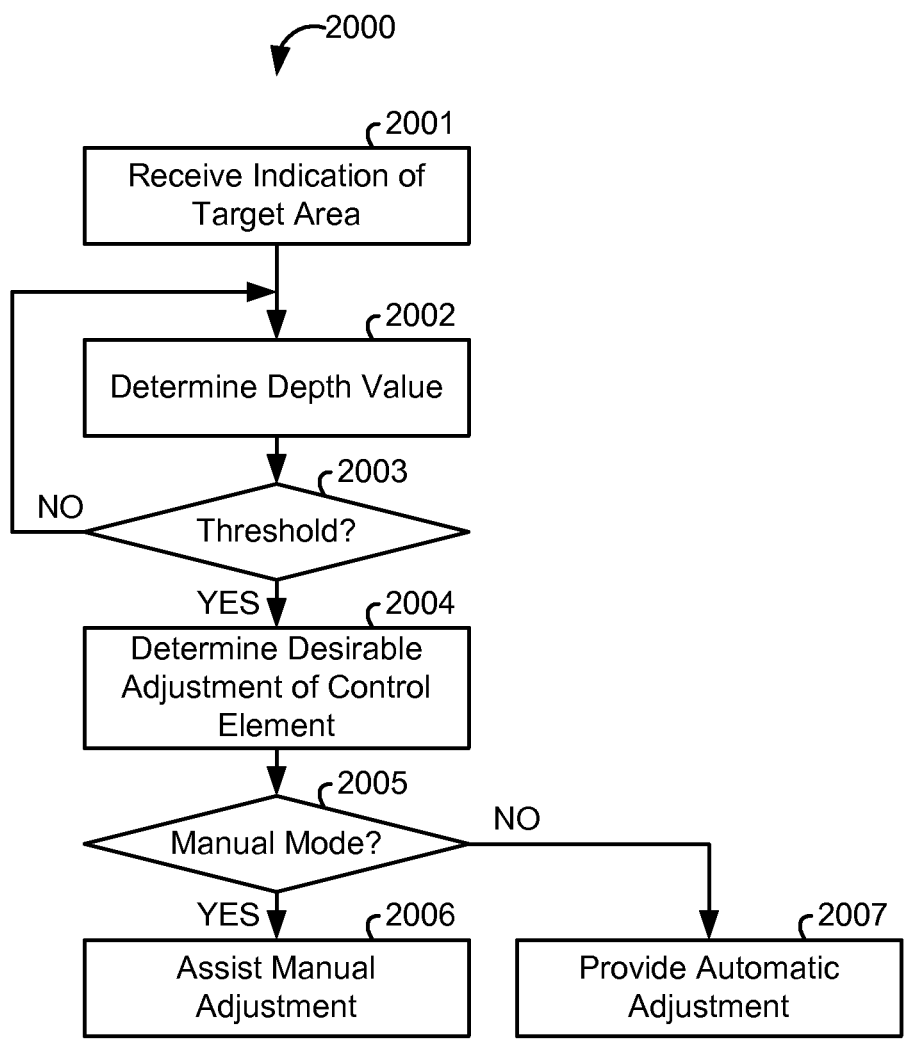
FIG. 2 illustrates a flow diagram of a method for intelligent manual adjustment of an image control element utilizing aspects of the present invention.

FIG. 2 illustrates, as an example, a flow diagram of a method 2000 for intelligent manual adjustment of an image control element. The method is preferably implemented as program code stored non-transitorily in memory 1033 and executed by the processor 1030. The image control element may be one of the control elements 1011, 1012, 1013 of the image capturing device 1010 or it may be one of the control elements 1021, 1022, 1023 of the viewer 1020.

Although the following description of the method describes adjustment of a single control element as a function of a depth value of a target area relative to an image capturing device, it is to be appreciated that the method may be extended and used to control any combination of multiple control elements as functions of multiple depth values for multiple target areas relative to multiple image capturing devices. FIGS. 3-13 are provided herein as part of, or to clarify with examples, the description of the method.

In block 2001, the method receives an indication of a target area (also referred to as a "region of interest"). As used herein, the target area may refer to an area in an image captured by the image capturing device 1010 as well as its corresponding area being displayed on the viewer 1020. Whether the term refers to a captured image or its corresponding displayed image should be clear from its contextual use. Although referred to as being an "area", the target area for stereovision is generally three-dimensional in shape and extends within a stereo view of the image capturing device to a surface topology of one or more objects.

The target area may be predefined as a default area in the images or it may be user defined or overridden. For example, the default area may be defined as a central area in the field of view of the image capturing device. As another example, the default area may be defined as an area on an object, wherein a central point of the area intersects a central line of sight of the image capturing device.

As an example of the user specifying a target area, the user may specify the target area on the viewer 1020 by interacting with the GUI 1041. As another example, the user may specify the target area by commanding movement of a cursor on the display screen of the viewer 1020 using a mouse and providing an indication that an area circumscribed by the movement of the cursor is to be selected as a target area by clicking a button on the mouse. When the target area is defined relative to the display screen of the viewer 1020, conventional transformation techniques are usable to translate the specified target area on the viewer 1020 to a corresponding target area in a reference frame defined by the image capturing perspective of the image capturing device 1010. For additional details on such reference frame transformations, see, e.g., U.S. 2012/0290134 A1 entitled "Estimation of a Position and Orientation of a Frame Used in Controlling Movement of a Tool," which is incorporated herein by reference.

As another example of the user specifying a target area, the user may specify the target area by using the telestrator 1044. As another example, the user may define the center of a target area using the gaze tracker 1043 which tracks the user's gaze point on the display screen of the viewer 1020. In this case, the user may select a target area by issuing a command to do so using, for example, one of the input devices 1031, 1032, wherein the center of the target area is the current gaze point and its area may be predefined or definable by the user using any conventional means such as the GUI 1041.

Regardless of how the target area is defined, it may be displayed for the convenience of the user on the viewer 1020 at its proper location as an overlay to any three-dimensional objects or surface topology being displayed thereon at the time. The overlay may be a three-dimensional overlay at the same depths and following the contour of the underlying objects or surface topology or it may be a two-dimensional overlay floating over the underlying objects or surface topology at a specified depth value.

In block 2002, the method determines the depth value for the target area in the stereo images using one or a combination of known methods. As an example, a structured light technique may be used in which a known light pattern is projected onto the target area and the relative light intensities on the scene tracked to derive a depth map for the scene. See, e.g., Daniel Scharstein and Richard Szeliski, "High-Accuracy Stereo Depth Maps Using Structured Light," IEEE Computer Society Conference on Computer Vision and Pattern Recognition (CVPR 2003), vol. 1, pages 195-202, Madison, Wis., June 2003. As another example, the depth value may be determined by determining corresponding points in stereo images using a robust sparse image matching algorithm, determining disparities between the corresponding points, and converting the disparities to depths using a predetermined disparity to depth mapping. See, e.g., U.S. Pat. No. 8,184,880 entitled "Robust Sparse Image Matching for Robotic Surgery", which is incorporated herein by reference. As yet another example, a laser range finder may be used for determining depth values of a three-dimensional scene. The depth value may be an average depth value for the surface topology of the target area. Alternatively, the depth value may be a minimum depth value for the surface topology of the target area. When tools, which are being used to interact with objects of the surface topology, appear above the surface topology, depth values for the tools which occlude part of the surface topology may be included or excluded from the calculation.

Figure 3:
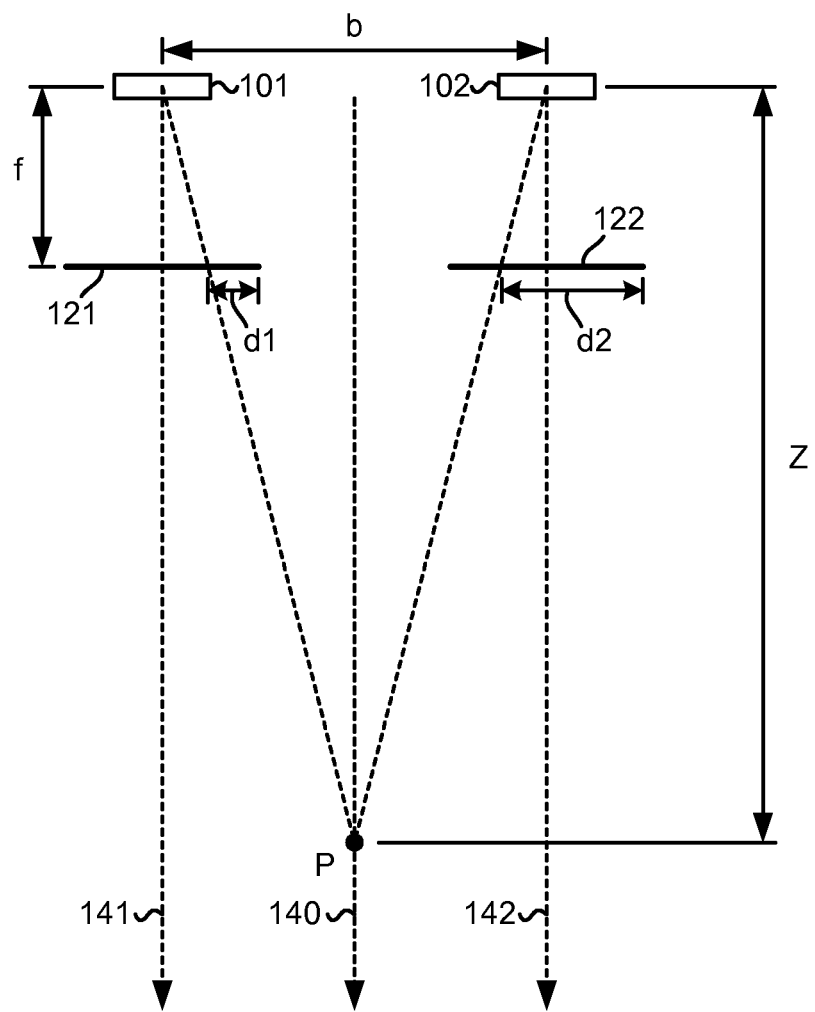
FIG. 3 illustrates a schematic of the stereo geometry for two image capturing elements of an imaging system utilizing aspects of the present invention.

As an example of the depth value, FIG. 3 illustrates a schematic of the stereo geometry for two image capturing elements, e.g., left and right optical lens 101, 102, which are separated by a baseline distance "b". Left and right image planes 121, 122 are shown at a focal length "f" (i.e., a depth at which the left and right images are focused). The image planes 121, 122 represent stereo images that are captured by the lens 101, 102 and are bounded by their fields of view. The focal length may be adjusted within a focusing range, but the baseline distance is fixed for the stereoscopic camera.

A point "P" at a depth "Z" from the lens 101, 102 is seen at different points on the image planes 121, 122. In particular, the point "P" is projected at a position "d1" on the left image plane 121 and projected at a position "d2" on the right image plane 122. The difference or disparity "D" between the two positions "d2" and "d1" can be determined from the following well-known relationship:

$$\frac{D}{b} = \frac{f}{Z} \quad (1)$$

Thus, as the depth "Z" gets smaller and smaller, the disparity "D" gets larger and larger.

Stereo images captured by the stereoscopic camera are displayable on a stereo viewer. As an example, the stereo viewer may have left and right display screens upon which left and right stereo images are respectively displayed. The stereo viewer in this case, may also have left and right eyepieces through which a user places his/her left and right eyes to respectively view the left and right display screens.

Figure 4:
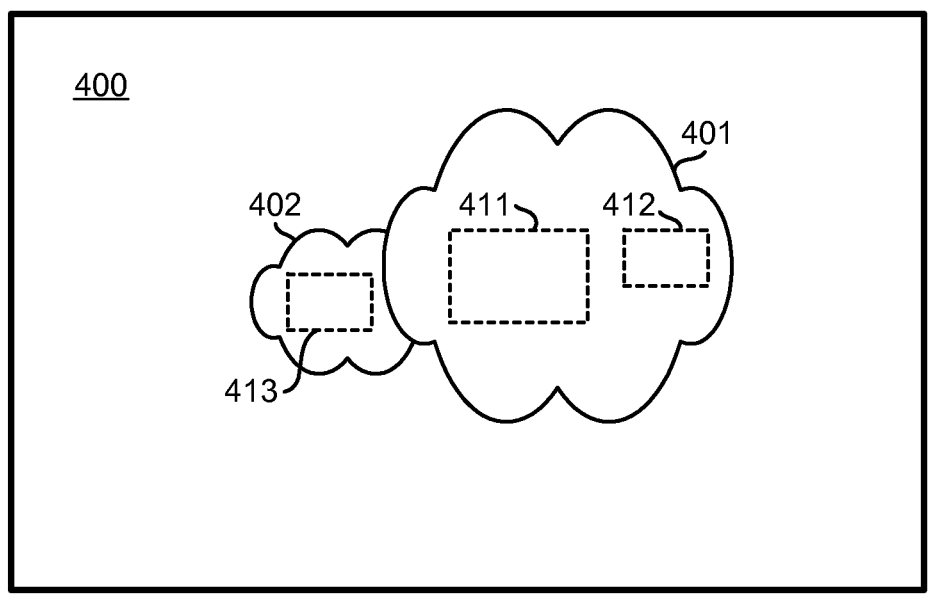
FIG. 4 illustrates a stereo view as seen in a stereo viewer of an imaging system utilizing aspects of the present invention.

Although use of a single target area is described above, it is to be appreciated that a plurality of target areas, each indicating a different area of interest, may be defined by a user and used in the method. In such case, one of the target areas may be selected for processing as described above. Alternatively, depth values may be determined for each of the plurality of target areas. In this alternative case, one of the depth values may then be selected and processed as described above or the depth values for a combination of target areas may be used instead, such as an average of the depth values. As an example of such a plurality of target areas, FIG. 4 illustrates a plurality of user specified target areas (e.g., 411, 412, 413) which have been defined relative to one or more objects (e.g., 401, 402) as seen on a two-dimensional or three-dimensional display screen 400 of the viewer 1020.

In block 2003, the method determines whether the depth value is less than a threshold depth value at which point an adjustment to the control element is desirable. The threshold depth value may be empirically determined and pre-programmed into or stored in the memory 1033 of the imaging system 1000 as a default value, such as three centimeters which has been empirically determined to be suitable for a medical robotic system as described in reference to FIGS. 7-10. Alternatively, the threshold depth value may be a function of a characteristic of an image captured by the image capturing device 1010. Additionally, or alternatively, it may be specified and/or altered by the user in a conventional manner to accommodate specific user preferences.

Although use of a single threshold depth value is described above, it is to be appreciated that a plurality of threshold depth values may be used in the method. For example, each threshold depth value may correspond to a different desirable adjustment for a control element. Alternatively, each threshold depth value may correspond to a desirable adjustment for a different control element.

If the determination in block 2003 is NO, then the method jumps back to block 2002 and loops through blocks 2002, 2003 until either a YES determination results in block 2003 or the method is turned OFF through a mode switch or some other means. If the determination in block 2003 is YES, the method proceeds to block 2004.

In block 2004, the method determines a desirable adjustment for the control element. As an example, the method may determine the desirable adjustment by using an empirically determined equation which is a function of depth values. The equation in this case may be included in program code stored in memory 1033 and executed by the processor 1030. As another example, the method may determine the desirable adjustment by using a Look-Up Table (LUT) of empirically determined values which is indexed by depth values. The LUT in this case may be stored in memory 1033 and accessed by the processor 1030 when performing the method. When using the LUT, a linear or best curve fitting interpolation between look-up table values may also be performed as necessary. Also, when using the LUT, the method may process the information read from the LUT by adjusting the information according to predefined and/or user specified preferences. Either or both the threshold value which is being used and the desirable adjustment which is being determined depend upon the characteristic of the image which is being adjusted by the control element. Typical controllable image characteristics include brightness, focus, contrast, resolution, color balance, and sharpness. These and other controllable characteristics of the image captured by the image capturing device 1010 or the image displayed on the viewer 1020 are to be included within the scope of the method.

As an example, when the image capturing device is a camera and the characteristic being controlled is the brightness of the captured image, the control element is the brightness control of the camera. In this case, the brightness control may be coupled to, or comprise, an adjustable gain of an image sensor of the camera or the brightness control may be coupled to, or comprise, an adjustable power output for an illuminator of the camera. The adjustment to the brightness control may be determined by the method using a function in which the brightness level monotonically decreases as the depth value changes from the threshold depth value to a minimum depth value (i.e., at very close range to the camera). The rate at which the brightness level monotonically decreases as the depth value changes from the threshold level to the minimum depth value may in this case be a function of a characteristic of the image captured by the camera. The characteristic being used in this case, may be any suitable one of the image characteristics previously mentioned.

As another example, when the image capturing device is a camera and the characteristic being controlled is the focus of the captured image, the control element may be a manually rotatable control, such as a knob or dial, which is used to adjust the focus of the camera. In this case, the desirable adjustment to the focus control may be determined as a function of a focal point of the camera and the depth value of the target area relative to the camera. In addition, an image characteristic of a captured image may be determined by the method and the desirable adjustment to the control element may be determined by modulating the output of a function of the depth value of the target area by the determined image characteristic.

In block 2005, the method determines whether it is operating in a manual mode. As an example, the default mode for the imaging system 1000 may be to perform an autofocus function. In this case, a manual over-ride must be activated by the user in order for the user to manually focus the image capturing device. Alternatively, the default mode for the imaging system 1000 may be the manual mode. In this latter case, the user must do something to initiate the autofocus mode such as depressing a button partially down such as on a camera. If the determination in block 2005 is YES, then the method proceeds to block 2006 where the method provides assistance to the user to manually adjust the control element to the desirable adjustment of the control element. On the other hand, if the determination in block 2005 is NO, then the method proceeds to block 2007 where the method automatically adjusts the control element to the desirable adjustment of the control element.

An example of processing performed by the method in block 2006 follows. If the image capturing device is a camera, if the characteristic being controlled is the focus of the captured image, and if the control element is a manually rotatable control, then in addition to determining the desirable adjustment to the focus control as previously described, a direction to the desirable adjustment may also be determined in block 2004. In this case, the direction of the adjustment may be determined by the direction that the camera is moving at the time relative to the target area.

Figure 5:
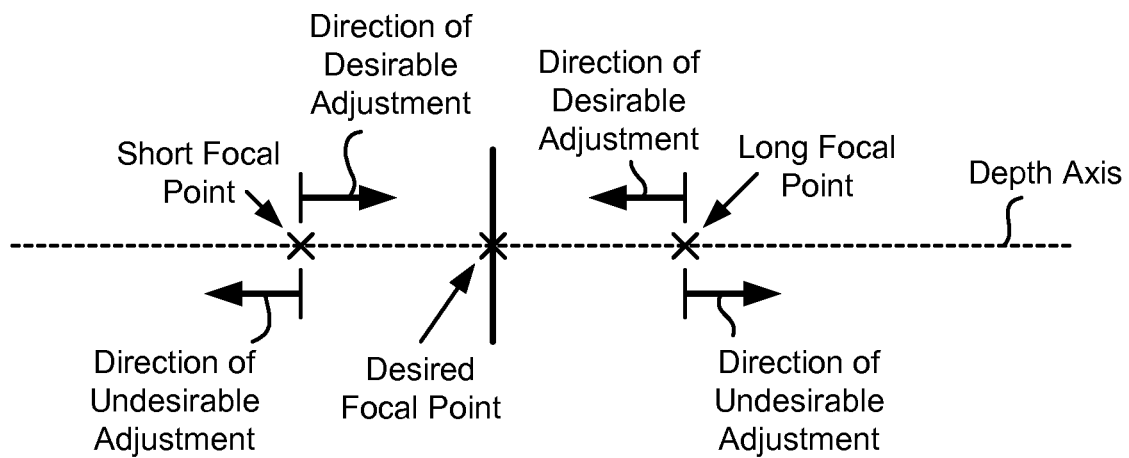
FIG. 5 illustrates a schematic of positions of a focal point along a depth axis relative to a desired focal point as may be experienced in an imaging system utilizing aspects of the present invention.

In particular, if prior to the movement, the focal point of the camera was properly adjusted to the depth value of the target area (i.e., a depth value which is referred to herein as the "Desired Focal Point"), then moving the camera towards the target area would result in moving the camera's focal point past the Desired Focal Point, such as the point designated as the "Long Focal Point" in FIG. 5. On the other hand, moving the camera back away from the target area would result in moving the focal point short of the Desired Focal Point, such as the point designated as the "Short Focal Point" in FIG. 5. Thus, the desirable adjustment of the focus control would result in moving a Long Focal Point back to the Desired Focal Point and moving a Short Focal Point forward to the Desired Focal Point, as shown by the arrows designated "Direction of Desirable Adjustment" in FIG. 5. In contrast, an undesirable adjustment of the focus control would result in moving further away from the Desired Focal Point, as shown by the arrows designated "Direction of Undesirable Adjustment" in FIG. 5.

The direction in which the camera is moving may be readily determined if the camera is moved by a robotic arm, such as described in reference to the endoscope of the medical robotic system 7000 of FIGS. 7-10. In that case, the direction of the camera movement may be determined by receiving sensor information indicating positions of joints of the robotic arm and determining the movement of the camera by applying the sensor information to forward kinematics of the robotic arm.

Figure 6:
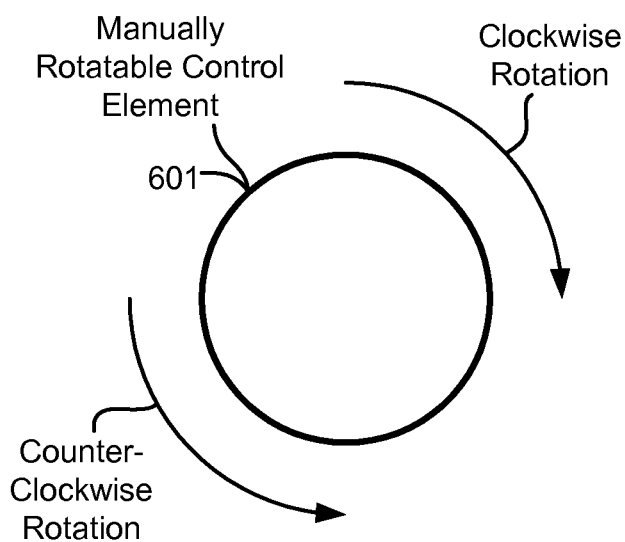
FIG. 6 illustrates a schematic of a manually rotatable control element of an imaging system utilizing aspects of the present invention.

Continuing with the example for block 2006, the method controls adjustment of the control element to assist manual adjustment of the control element to the desirable adjustment by providing assistance to manually adjust the focus control according to the determined direction and the amount of the desirable adjustment determined in block 2004. One way such assistance may be provided is to define a rotation direction of a manually rotatable control to always correspond to moving the focal point towards the depth value of the target area and an opposite rotation direction of the manually rotatable control to always correspond to moving the focal point away from the depth value of the target area. As an example, the method may provide assistance to manually adjust the focus control by defining a Clockwise Rotation of the manually rotatable control element 601 (as shown in FIG. 6) as always resulting in moving the focal point towards the Desired Focal Point in the Direction of Desirable Adjustment (as shown in FIG. 5) and defining a Counter-Clockwise Rotation of the manually rotatable control element 601 (as shown in FIG. 6) as always resulting in moving the focal point away from the Desired Focal Point in the Direction of Undesirable Adjustment (as shown in FIG. 5). In this case, the user does not need to know whether the focal point of the camera is short or long of the Desired Focal Point. In either case, a Clockwise Rotation of the of the manually rotatable control element 601 will drive the focal point towards the Desired Focal Point.

Still continuing with the example for block 2006, another way such assistance may be provided is to define a rotation direction of a manually rotatable control that the user first takes as corresponding to moving the focal point towards the depth value of the target area and an opposite rotation direction of the manually rotatable control as corresponding to moving the focal point away from the depth value of the target area. As an example, the method provides assistance to manually adjust the focus control by defining a Clockwise Rotation of the manually rotatable control element 601 (as shown in FIG. 6) as resulting in moving the focal point towards the Desired Focal Point in the Direction of Desirable Adjustment (as shown in FIG. 5) if the user first rotates the manually rotatable control element 601 in the clockwise direction while the method is performing block 2006. In this case, if the user subsequently rotates the manually rotatable control element 601 in the counter-clockwise direction while the method is performing block 2006, it will result in the focal point moving in the Direction of the Undesirable Adjustment (as shown in FIG. 5). Conversely, if the user first rotates the manually rotatable control element 601 in the counter-clockwise direction while the method is performing block 2006, then the method provides assistance to manually adjust the focus control by defining a Counter-Clockwise Rotation of the manually rotatable control element 601 (as shown in FIG. 6) as resulting in moving the focal point towards the Desired Focal Point in the Direction of Desirable Adjustment (as shown in FIG. 5). In this latter case, if the user subsequently rotates the manually rotatable control element 601 in the clockwise direction while the method is performing block 2006, it will result in the focal point moving in the Direction of the Undesirable Adjustment (as shown in FIG. 5).

For additional assistance in manually adjusting the control element to the desirable adjustment in block 2006, the method may provide a sensory indication when the focal point of an image capturing device, such as a camera, coincides with the target point. The sensory indication may be one or more of a visual indication on the viewer 1020, an auditory indication on the speaker 1042, and a force feedback on the manually rotatable control element 601. The force feedback is preferably a haptic force on the control element that nudges the user to move the control element to the desirable adjustment so that the focal point of the imaging device is moved to coincide with the depth value of the target area. In such case, the haptic force may decrease in magnitude as the focal point of the imaging device moves closer towards the Desired Focal Point and may increase in magnitude as the focal point of the imaging device moves further away from the Desired Focal Point.

Automatic processing such as performed by the method in block 2007 is relatively straightforward. Examples of such automatic processing include the autofocus and automatic exposure functions on a camera. Basically, they simply entail controlling adjustment of the control element automatically to the desirable adjustment if the control element is to be automatically adjusted.

Figure 7:
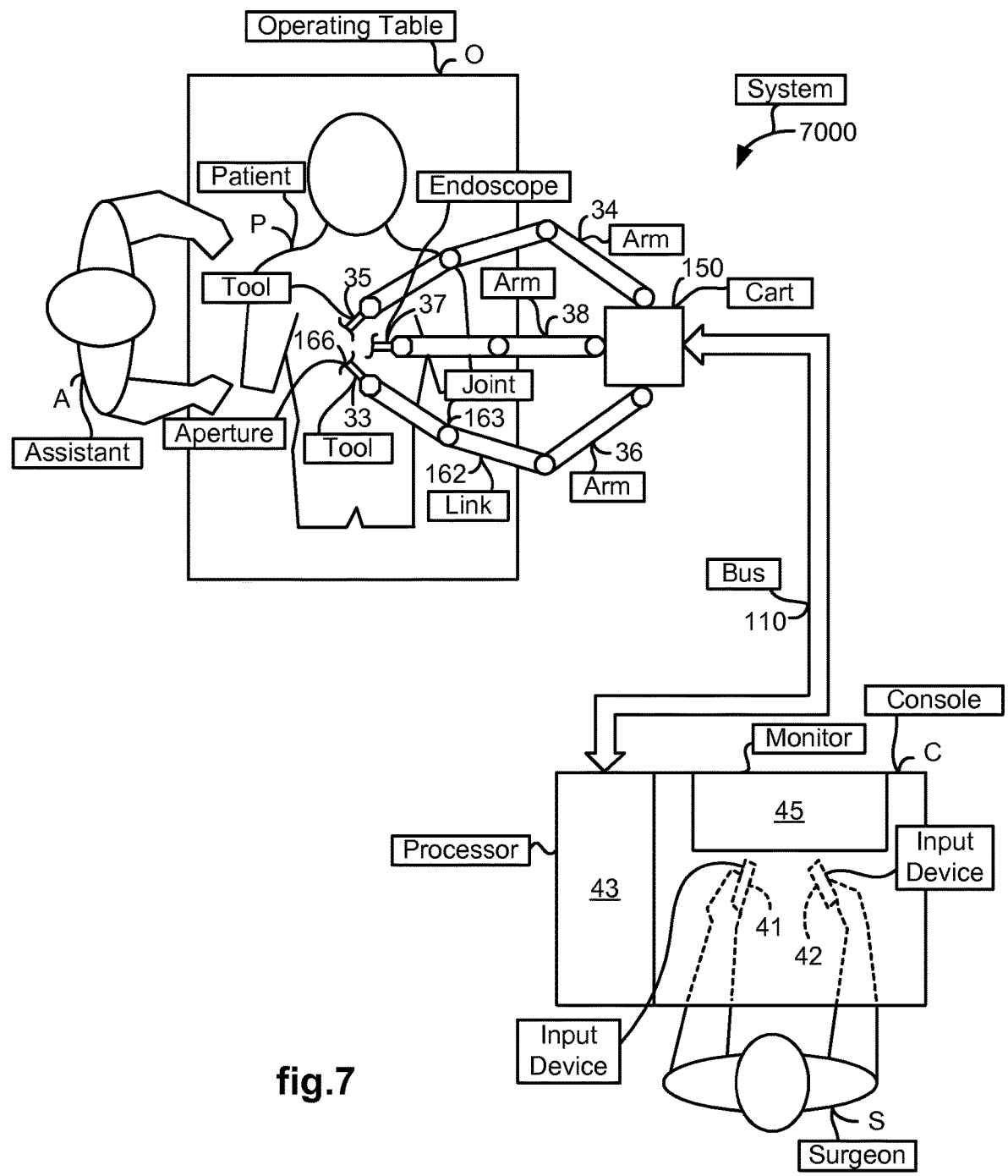
FIG. 7 illustrates a top view of an operating room employing a medical robotic system including an imaging system utilizing aspects of the present invention.

FIGS. 7-10 illustrate, as an example, a medical robotic system 7000 in which the method 2000 may be implemented and the imaging system 1000 may be included. FIG. 7 illustrates a top view of an operating room in which the medical robotic system 7000 is being employed by a Surgeon ("S") to perform a medical procedure on a Patient ("P"). The medical robotic system in this case is a Minimally Invasive Robotic Surgical (MIRS) system including a Console ("C") utilized by the Surgeon while performing a minimally invasive diagnostic or surgical procedure on the Patient with assistance from one or more Assistants ("A") while the Patient is on an Operating table ("O"). The medical robotic system 7000 may include the imaging system 1000 or it may be considered a particular example of the imaging system 1000.

Figure 10:
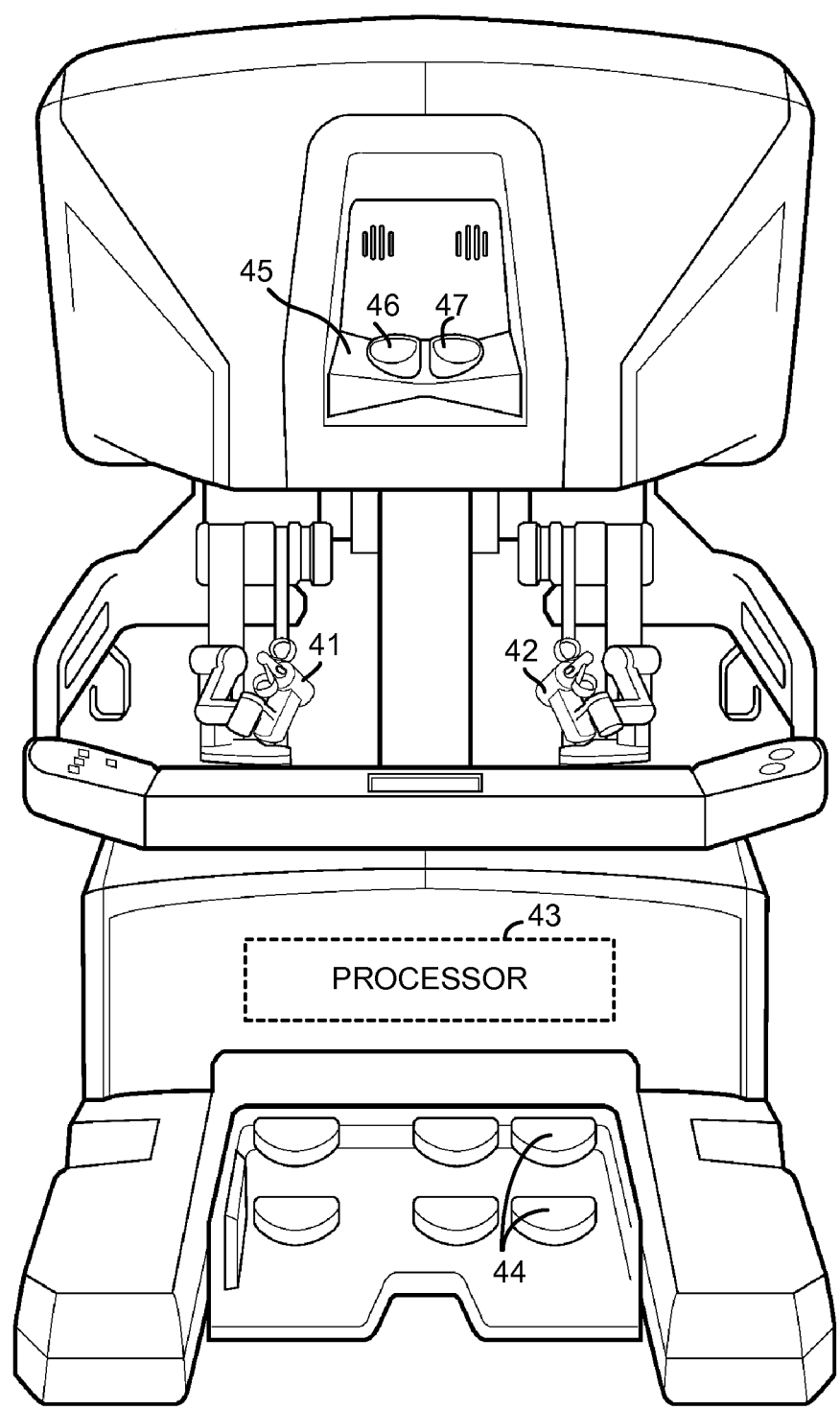
FIG. 10 illustrates a front view of an operator console usable in a medical robotic system including an imaging system utilizing aspects of the present invention.

The Console, as further described in reference to FIG. 10, includes a processor 43 which communicates with a movable cart 150 over a bus 110. A plurality of robotic arms 34, 36, 38 are included on the cart 150. A tool 33 is held and manipulated by robotic arm 36, another tool 35 is held and manipulated by robotic arm 34, and an endoscope 37 is held and manipulated by robotic arm 38. In this example, each of the tools 33, 35 and the endoscope 37 is introduced through its own entry aperture in the Patient. As an example, tool 33 is inserted into aperture 166 to enter the Patient.

The Surgeon performs the medical procedure by manipulating the input devices 41, 42 so that the processor 43 causes their respectively associated robotic arms 34, 36 to manipulate their respective removably coupled tools 33, 35 accordingly while the Surgeon views real-time images of a work site in three-dimensions ("3D") on a stereo vision display 45 of the Console. A stereoscopic endoscope 37 (having left and right cameras for capturing left and right stereo views) captures stereo images of the work site. The processor 43 processes the stereo images so that they may be properly displayed on the stereo vision display 45.

Each of the robotic arms 34, 36, 38 is conventionally formed of links, such as link 162, which are coupled together and manipulated through actuatable joints, such as joint 163. Each of the robotic arms includes a setup arm and a slave manipulator. The setup arm positions its held tool so that a pivot point occurs at its entry aperture into the Patient. The slave manipulator may then manipulate its held tool or endoscope so that it may be pivoted about the pivot point, inserted into and retracted out of the entry aperture, and rotated about its shaft axis. The robotic arms 34, 36, 38 may be carted into the operating room via the cart 150 or alternatively, they may be attached to sliders on a wall or ceiling of the operating room.

Figure 8:
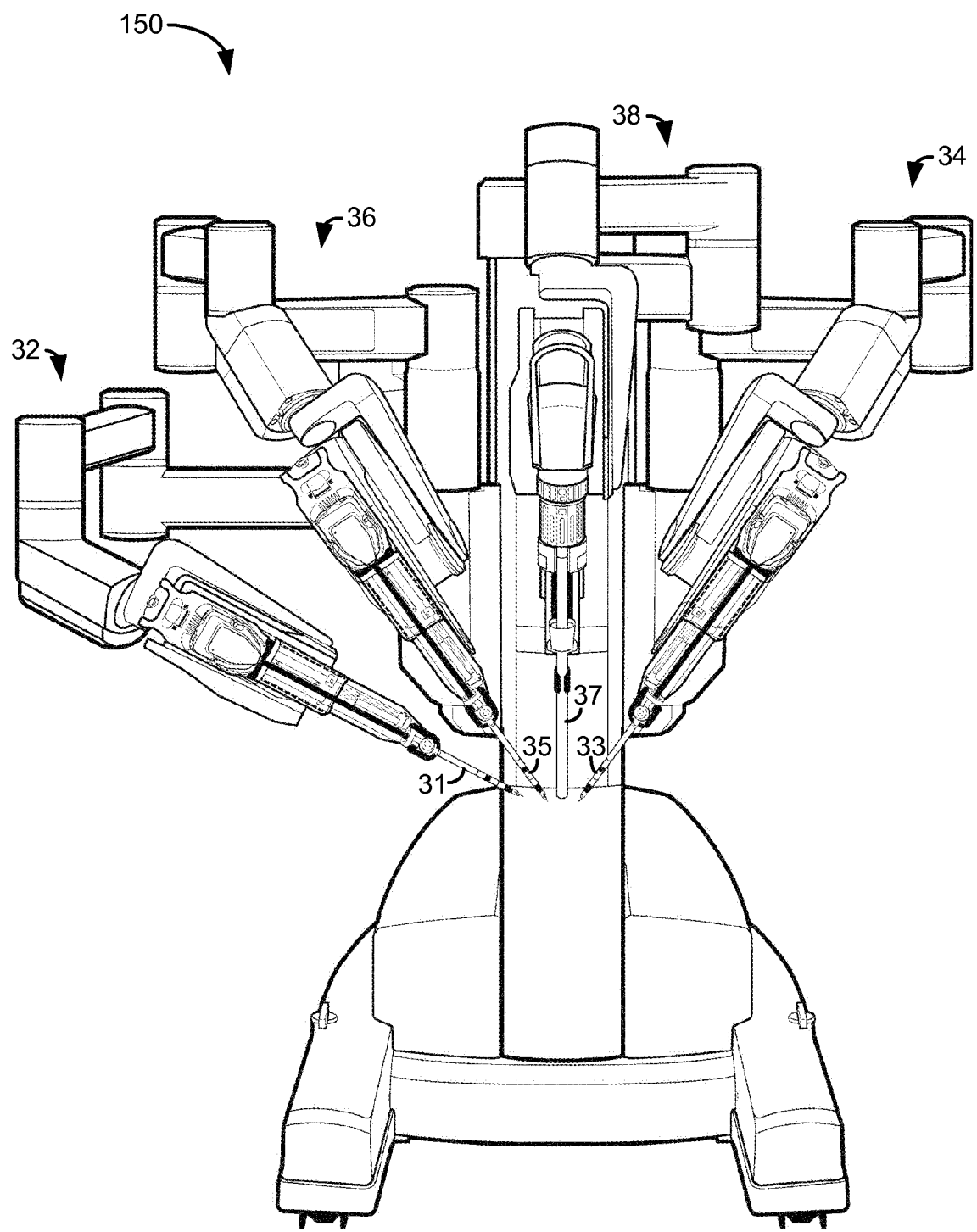
FIG. 8 illustrates a side view of a patient-side cart usable in a medical robotic system including an imaging system utilizing aspects of the present invention.

FIG. 8 illustrates a front view of the cart 150. In addition to the robotic arms 34, 36, 38, shown in FIG. 7, a fourth robotic arm 32 is shown in FIG. 8. The fourth robotic arm 32 is available so that another tool 31 may be introduced at the work site along with the tools 33, 35 and endoscope 37.

Figure 9:
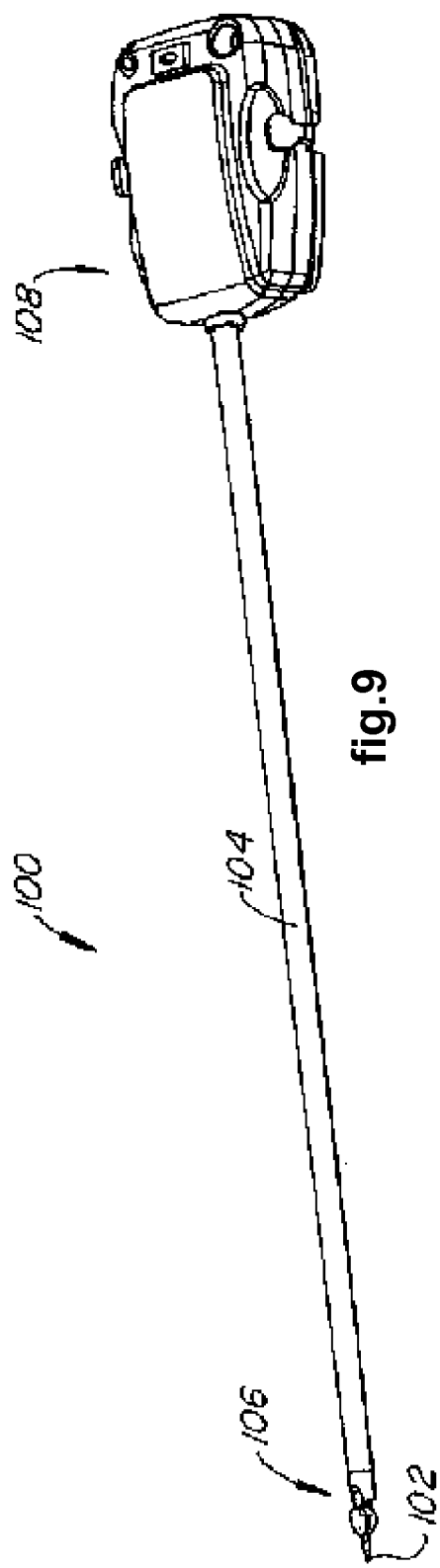
FIG. 9 illustrates a perspective view of an instrument usable in a medical robotic system including an imaging system utilizing aspects of the present invention.

FIG. 9 illustrates an exemplary tool 100 that may be used for either tool 33 or 35. The tool 100 comprises an interface housing 108, a shaft 104, an end effector 102, and a wrist mechanism 106 which includes one or more wrist joints. The interface housing 108 is removably attached to a robotic arm so as to be mechanically coupled to actuators (such as motors) in the slave manipulator of the attached robotic arm. Cables or rods, that are coupled to the actuators of the slave manipulator and extend through the shaft 104 from the interface housing 108 to the one or more wrist joints of the wrist mechanism 106 and to the jaws of the tool's end effector 102, actuate the wrist joints and jaws in a conventional manner. The slave manipulator may also manipulate the tool in pitch and yaw angular rotations about its pivot point at the entry aperture, manipulate the tool in a roll angular rotation about the tool's shaft axis, and insert and retract the tool along a rail on the robotic arm as commanded by the processor 43.

FIG. 10 illustrates, as an example, a front view of the Console usable in the medical robotic system 1000. The Console has left and right input devices 41, 42 which the user may grasp respectively with his/her left and right hands to manipulate associated devices, such as the tools 33, 35, in preferably six degrees-of-freedom ("DOF"). Foot pedals 44 with toe and heel controls are provided on the Console so the user may control movement and/or actuation of devices associated with the foot pedals. A processor 43 is provided in the Console for control and other purposes. The stereo vision display 45 is provided so that the user may view the work site in stereo vision from images captured by the stereoscopic camera of the endoscope 37. Left and right eyepieces, 46 and 47, are provided in the stereo vision display 45 so that the user may view left and right two-dimensional ("2D") display screens inside the display 45 respectively with the user's left and right eyes.

The processor 43 performs various functions in the medical robotic system. One important function that it performs is to translate and transfer the mechanical motion of input devices 41, 42 through control signals over bus 110 to command actuators of their associated robotic arms to actuate their respective joints so that the Surgeon can effectively manipulate devices, such as the tools 33, 35, and endoscope 37. Another function is to perform the method 2000 as well as implement various controllers and/or other methods described herein. Although described as a processor, it is to be appreciated that the processor 43 may be implemented by any combination of hardware, software and firmware. Also, its functions as described herein may be performed by one unit or divided up among different components, each of which may be implemented in turn by any combination of hardware, software and firmware. Further, although being shown as part of or being physically adjacent to the Console, the processor 43 may also comprise a number of subunits distributed throughout the system.

U.S. Pat. No. 6,659,939 B2 entitled "Cooperative Minimally Invasive Telesurgical System," which is incorporated herein by reference, provides additional details on a medical robotic system such as described herein.

Figure 11:
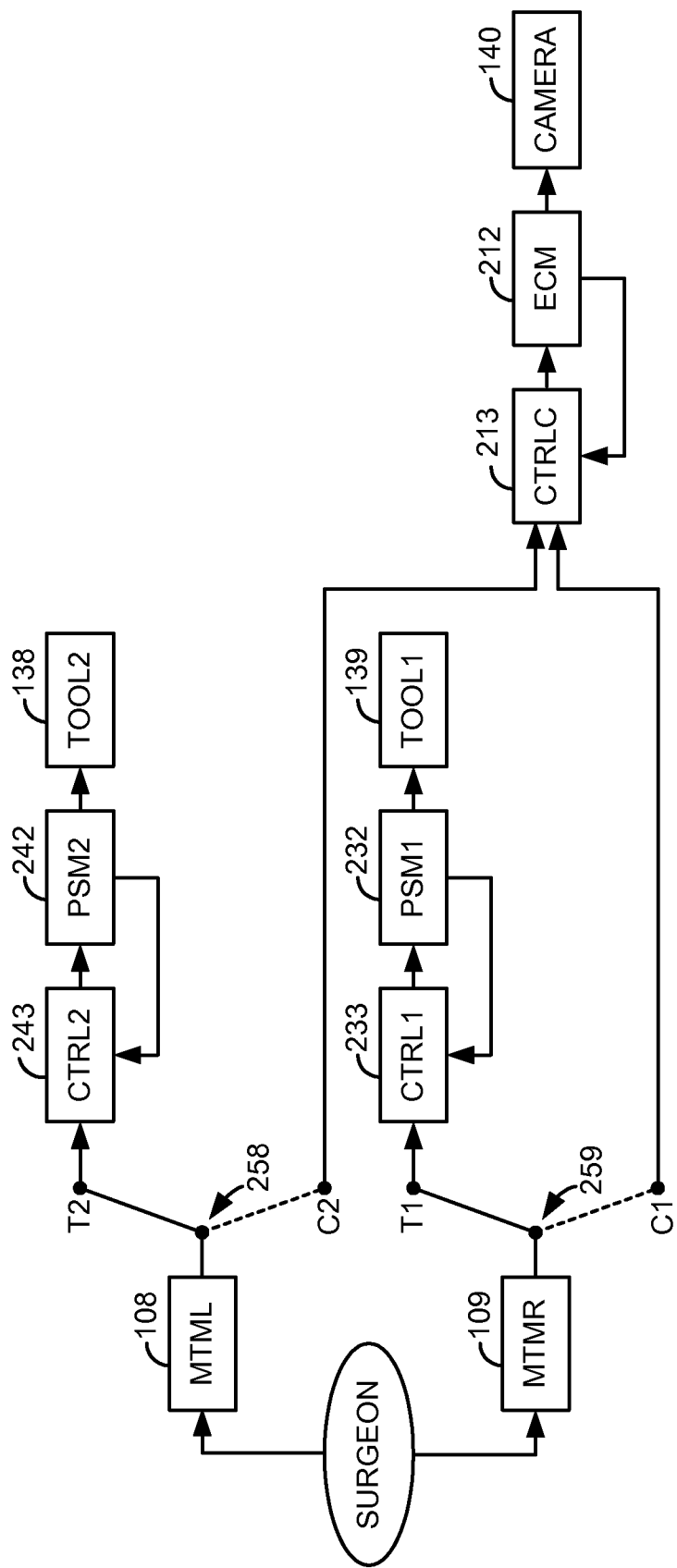
FIG. 11 illustrates a block diagram of the medical robotic system including an imaging system utilizing aspects of the present invention.

FIG. 11 illustrates, as an example, a block diagram of components for controlling and selectively associating device manipulators to the master controls 108, 109. Various surgical tools such as graspers, cutters, and needles may be used to perform a medical procedure at a work site within the Patient. In this example, two surgical tools 138, 139 are used to robotically perform the procedure and the camera 140 is used to view the procedure.

Each of the medical devices 138, 139, 140 is manipulated by its own manipulator. In particular, the camera 140 is manipulated by a camera manipulator (ECM) 212, the first surgical tool 139 is manipulated by a first tool manipulator (PSM1) 232, and the second surgical tool 138 is manipulated by a second tool manipulator (PSM2) 242.

In this example, each of the master controls 108, 109 may be selectively associated with either the camera 140 or one of the surgical tools 138, 139 so that the associated device may be controlled by the input device through its controller and manipulator. For example, by placing switches 258, 259 in their respective tool following modes "T2" and "T1", the left and right master controls 108, 109 may be respectively associated with the surgical tools 139, 138, which are telerobotically controlled through their respective controllers 233, 243 and manipulators 232, 242 so that the Surgeon may perform a medical procedure on the Patient while the camera 140 is soft-locked in place by its controller 213.

When the camera 140 is to be repositioned by the Surgeon, either one or both of the left and right master controls 108, 109 may be associated with the camera 140 so that the Surgeon may move the camera 140 through its controller 213 and manipulator 212. In this case, the disassociated one(s) of the surgical tools 138, 139 is/are soft-locked in place by its/their controller(s). For example, by placing switches 258, 259 respectively in camera positioning modes "C2" and "C1", the left and right master controls 108, 109 may be associated with the camera 140, which is telerobotically controlled through its controller 213 and manipulator 212 so that the Surgeon may position the camera 140 while the surgical tools 138, 139 are soft-locked in place by their respective controllers 233, 243. If only one input device is to be used for positioning the camera, then only one of the switches 258, 259 is placed in its camera positioning mode while the other one of the switches 258, 259 remains in its tool following mode so that its respective input device may continue to control its associated surgical tool.

The selective association of the master controls 108, 109 to other devices in this example may be performed by the Surgeon using a Graphical User Interface (GUI), a voice recognition system, or any other conventional manner operable through the Surgeon Console. Alternatively, the association of the master controls 108, 109 may be changed by the Surgeon depressing a button on one of the master controls 108, 109 or depressing the foot pedal 105, or using any other well known mode switching technique.

One application in which the present invention is particularly useful is when the switches 258, 259 are both placed in their respective camera positioning modes "C2" and "C1" and an "image referenced control" scheme is employed to control Surgeon positioning and orienting of the camera's tip using the master controls 108, 109 in a "virtual handlebar" fashion.

Figure 12:
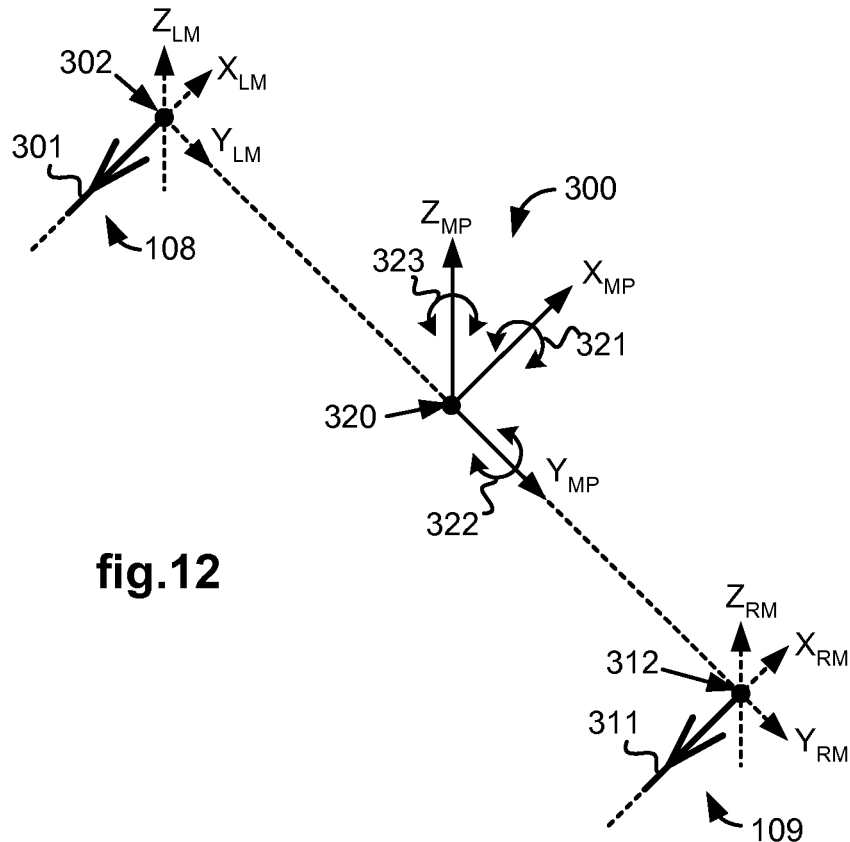
FIG. 12 illustrates master control device reference frames and corresponding degrees of freedom in a medical robotic including an imaging system utilizing aspects of the present invention.

FIG. 12 illustrates, as an example, reference frames and corresponding degrees-of-freedom for the master controls 108, 109. Each of the master controls 108, 109 has a respective pivot point 302, 312 (also referred to as a "control point") and a reference frame centered at the pivot point. The master controls 108, 109 provide three translational degrees-of-freedom movement (e.g., forward/back along their respective longitudinal axes $X_{LM}$, $X_{RM}$ of their grippers 301, 311; side-to-side along first axes $Y_{LM}$, $Y_{RM}$ orthogonal to the longitudinal axes $X_{LM}$, $X_{RM}$; and up/down along second axes $Z_{LM}$, $Z_{RM}$ orthogonal to the first axes $Y_{LM}$, $Y_{RM}$ and longitudinal axes $X_{LM}$, $X_{RM}$) relative to their respective pivot points 302, 312 of their grippers 301, 311. The master controls 108, 109 also provide three orientational degrees-of-freedom movement (e.g., roll about their respective longitudinal axes $X_{LM}$, $X_{RM}$; pitch about their respective first axes $Y_{LM}$, $Y_{RM}$; and yaw about their respective second axes am, $Z_{RM}$) relative to their respective pivot points 302, 312 of their grippers 301, 311. In addition, squeezing their respective grippers 301, 311 may provide additional degrees-of-freedom for manipulating end effectors of surgical tools respectively associated with the master controls 108, 109 when in tool following mode.

In this example, both master controls 108, 109 are used to move the camera 140 as the Surgeon views images captured by the camera 140. Thus, an "image referenced control" is used in which the Surgeon is given the impression that he or she is moving the image captured by the camera 140. In particular, the Surgeon is provided with the sensation that he or she is grasping the image being displayed on the monitor 104 with his or her left and right hands and moving the image about the work site to a desired viewing point.

Figure 13:
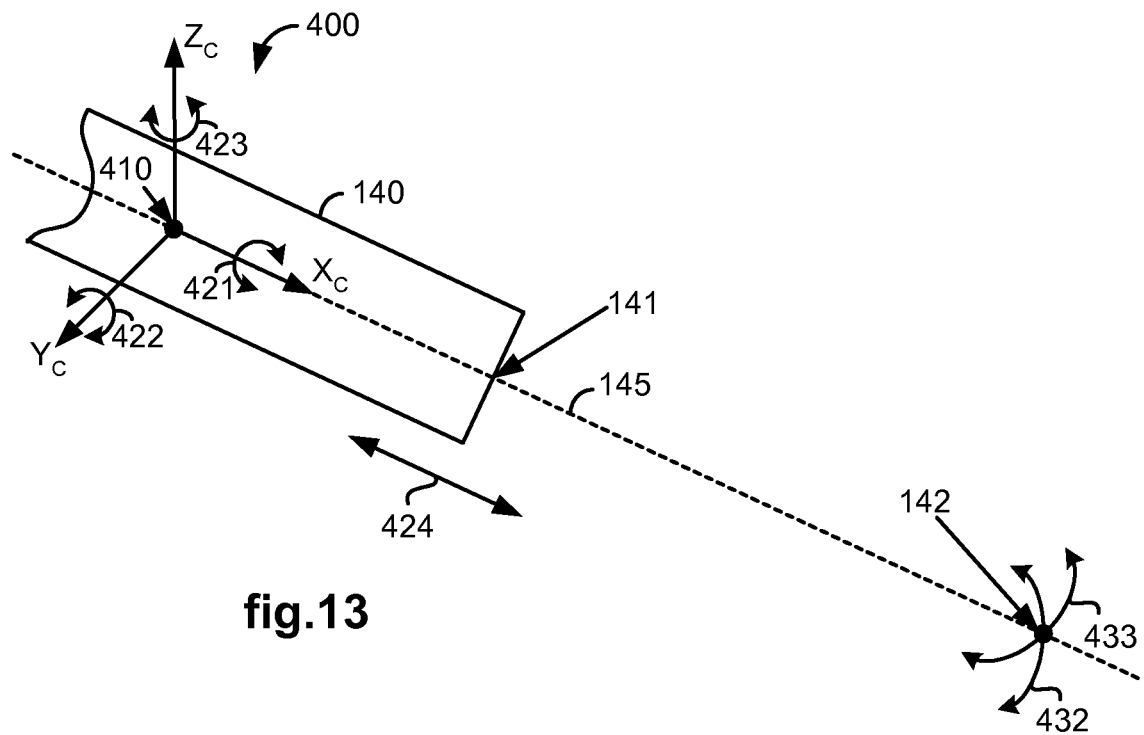
FIG. 13 illustrates a camera control reference frame and corresponding degrees of freedom in a medical robotic including an imaging system utilizing aspects of the present invention.

FIG. 13 illustrates, as an example, a reference frame 400 and corresponding degrees-of-freedom for controlling movement of a tip of the camera 140. In this case, the camera tip 141 may be pivoted about a pivot point 410 (also referred to as a "fulcrum" and "remote center") in roll 421 about an axis $X_C$ extending along a longitudinal axis 145 of the camera 140 and/or its entry guide (not shown), in pitch 422 about an axis $Y_C$ (which is orthogonal to the $X_C$ axis), and in yaw 423 about an axis $Z_C$ (which is orthogonal to both the $X_C$ and $Y_C$ axes), as well as inserted/retracted 424 along the longitudinal axis 145 by operation of the camera manipulator 212 so as to provide four degrees-of-freedom movement. The longitudinal axis 145 centrally extends through the proximal and distal ends of the camera 140. A focal point 142 of the camera 140 moves along a surface of a sphere (having a radius defined by the insertion distance of the camera tip 141 from the remote center 410 and the focal length) as the camera tip 141 is moved in pitch and yaw (i.e., along arc 432 when the camera tip 141 is moved in pitch 422 and along arc 433 when the camera tip 141 is moved in yaw 423).

To control movement in the four degrees-of-freedom of the camera tip 141, a "virtual handlebar" scheme using the pair of master controls 108, 109 is used in which the two master controls are constrained to move together in a prescribed manner. Referring to FIG. 12, the "virtual handlebar" employs a reference frame 300 having its origin at a mid-point 320 which is half-way between the pivot points 302, 312 of the master controls 108, 109. The Y-axis $Y_{MP}$ of the frame 300 is along a line intersecting the pivot points 302, 312, the Z-axis $Z_{MP}$ is in a vertical direction orthogonal to the Y-axis $Y_{MP}$, and the X-axis $X_{MP}$ is in a forward/back direction that is orthogonal to both the Y-axis $Y_{MP}$ and the Z-axis $Z_{MP}$.

The "virtual handlebar" reference frame 300 is related to the camera control reference frame 400 so that movement relative to the mid-point 320 by the master controls 108, 109 results in movement of the camera tip 141 relative to the remote center 410. In particular, as the mid-point 320 is moved forward/back in the $X_{MP}$ direction by moving both master controls 108, 109 forward/back, the camera controller 213 commands the camera manipulator 212 to move the camera 140 forward/back in the $X_C$ direction. Also, as the left master control 108 is moved up/down and the right master control 109 is moved in an opposite direction relative to the $Z_{MP}$ axis, the camera controller 213 commands the camera manipulator 212 to rotate the camera 140 in roll about the $X_C$ axis. Further, as the left master control 108 is moved forward/back and the right master control 109 is moved in an opposite direction relative to the $X_{MP}$ axis, the camera controller 213 commands the camera 140 to rotate in yaw about the $Z_C$ axis. Finally, as both the left and right master controls 108, 109 are pivoted together about their respective pivot points 302, 312 in the same direction, the camera controller 213 commands the camera manipulator 212 to rotate the camera 140 in pitch about the $Y_C$ axis.

Note that in using the "virtual handlebar" scheme as described above there are several unused degrees-of-freedom for each of the master controls 108, 109. For example, the master roll for each master control is unused (i.e., rotation of its gripper about its X-axis). Since the gripper's master roll resembles a dial to the Surgeon, it potentially can be used to turn on and adjust an attribute of an image capturing device such as a camera's focus, zoom, brightness, contrast, etc., in a similar manner as a radio's volume dial may turn on the radio and adjust its volume. Thus, each gripper's master roll may be used as one of the control elements 1011, 1012, 1013, 1021, 1022, 1023. In this case, force feedback to the masters may be provided to serve as haptic feedback to the user to assist the user in manually adjusting the control element. Further, the imaging system 1000 may be implemented in the medical robotic system 7000 by the endoscope 37 functioning as the image capturing device 1010, the stereo vision display 45 functioning as the viewer 1020, and the processor 43 functioning as the processor 1030.

Although the various aspects of the present invention have been described with respect to a preferred embodiment, it will be understood that the invention is entitled to full protection within the full scope of the appended claims.

What is claimed is:

1. A method for automatic adjustment of a brightness control for images captured by an image capturing device, the method comprising:
    a processor determining a depth value of a target area relative to the image capturing device;
    the processor determining a desirable adjustment to the brightness control so that a brightness level of images captured by the image capturing device is lowered if the depth value of the target area relative to the image capturing device is less than a threshold depth value;
    the processor determining whether an adjustment of the brightness control is to be automatically or manually adjusted; and
    conditioned upon the processor determining that the adjustment of the brightness control is to be manually adjusted, the processor over-riding manual control of the brightness control if an operator of the brightness control is causing the brightness level of images captured by the image capturing device not to be lowered if the depth value of the target area relative to the image capturing device is less than the threshold depth value.

2. The method of claim 1, further comprising:
    conditioned upon the processor determining that the adjustment of the brightness control is to be automatically adjusted,
    the processor automatically controlling adjustment of the brightness control to the desirable adjustment.

3. The method of claim 1, further comprising:
    the processor determining the depth value as one of an average depth value and a minimum depth value for a surface topology of the target area.

4. The method of claim 1,
    wherein the image capturing device comprises a camera, and
    wherein the brightness control is coupled to one of an adjustable gain of an image sensor of the camera and an adjustable power output for an illuminator of the camera.

5. The method of claim 4,
    wherein the processor determining the desirable adjustment to the brightness control comprises:
    the processor determining the desirable adjustment to the brightness control such that the brightness level monotonically decreases as the depth value changes from the threshold depth value to a minimum depth value.

6. The method of claim 5,
    wherein the processor determining the desirable adjustment to the brightness control such that the brightness level monotonically decreases as the depth value changes from the threshold depth value to a minimum depth value comprises:
    the processor determining the desirable adjustment to the brightness control such that a rate that the brightness level monotonically decreases, as the depth value changes from the threshold depth value to the minimum depth value, is a function of a characteristic of an image captured by the camera.

7. The method of claim 4, wherein the threshold depth value is a function of a characteristic of an image captured by the camera.

8. The method of claim 1, wherein the target area is a default area unless overridden by an operator specified area.

9. The method of claim 1, wherein the processor determining the desirable adjustment to the brightness control comprises:
    the processor determining the desirable adjustment to the brightness control by using a look-up table indexed by depth values relative to the image capturing device.

10. An imaging system comprising:
    an image capturing device;
    a brightness control for images captured by the image capturing device; and
    a processor configured to:
        determine a depth value of a target area relative to the image capturing device;
        determine a desirable adjustment to the brightness control so that a brightness level of images captured by the image capturing device is lowered if the depth value of the target area relative to the image capturing device is less than a threshold depth value;
        determine whether an adjustment of the brightness control is to be automatically or manually adjusted; and
        over-ride manual control of the brightness control if the brightness control is to be manually adjusted and an operator of the brightness control is causing the brightness level of images captured by the image capturing device not to be lowered if the depth value of the target area relative to the image capturing device is less than the threshold depth value.

11. The imaging system of claim 10, wherein the processor is further configured to:
    control adjustment of the brightness control automatically to the desirable adjustment if the brightness control is to be automatically adjusted.

12. The imaging system of claim 10, wherein the processor is further configured to:
   determine the depth value as one of an average depth value and a minimum depth value for a surface topology of the target area.

13. The imaging system of claim 10,
   wherein the image capturing device comprises a camera, and
   wherein the brightness control is coupled to one of an adjustable gain of an image sensor of the camera and an adjustable power output for an illuminator of the camera.

14. The imaging system of claim 13, wherein the processor is further configured to:
   determine the adjustment to the brightness control so that the brightness level monotonically decreases as the depth value changes from the threshold depth value to a minimum depth value.

15. The imaging system of claim 14, wherein the processor is further configured to:
   determine the adjustment to the brightness control so that a rate that the brightness level monotonically decreases as the depth value changes from the threshold depth value to the minimum depth value is a function of a characteristic of an image captured by the camera.

16. The imaging system of claim 13, wherein the threshold depth value is a function of a characteristic of an image captured by the camera.

17. The imaging system of claim 10, wherein the target area is a default area unless overridden by an operator specified area.

18. The imaging system of claim 10, wherein the processor is further configured to:
   determine the desirable adjustment to the brightness control by using a look-up table indexed by depth values relative to the image capturing device.

* * * * *